(12) United States Patent
Parker

(10) Patent No.: US 9,955,270 B2
(45) Date of Patent: Apr. 24, 2018

(54) BONE CONDUCTION DEVICE FITTING

(75) Inventor: John Parker, Roseville (AU)

(73) Assignee: Cochlear Limited, Macquarie University, NSW (AU)

( * ) Notice: Subject to any disclaimer, the term of this patent is extended or adjusted under 35 U.S.C. 154(b) by 905 days.

(21) Appl. No.: 12/935,887

(22) PCT Filed: Mar. 31, 2009

(86) PCT No.: PCT/US2009/038890
§ 371 (c)(1),
(2), (4) Date: Sep. 30, 2010

(87) PCT Pub. No.: WO2009/124010
PCT Pub. Date: Oct. 8, 2009

(65) Prior Publication Data
US 2011/0022119 A1  Jan. 27, 2011

Related U.S. Application Data

(60) Provisional application No. 61/041,185, filed on Mar. 31, 2008.

(51) Int. Cl.
*A61N 1/00* (2006.01)
*H04R 25/00* (2006.01)
*A61M 5/142* (2006.01)

(52) U.S. Cl.
CPC ........... *H04R 25/00* (2013.01); *H04R 25/606* (2013.01); *H04R 25/70* (2013.01); *A61M 5/14276* (2013.01); *A61M 2205/05* (2013.01); *A61M 2210/0662* (2013.01); *H04R 2460/13* (2013.01); *Y10T 29/49572* (2015.01)

(58) Field of Classification Search
CPC ............................ A61N 1/0526; A61N 1/0541
See application file for complete search history.

(56) References Cited

U.S. PATENT DOCUMENTS

| | | |
|---|---|---|
| 3,809,829 A | 5/1974 | Vignini et al. |
| 5,323,468 A | 6/1994 | Bottesch |
| 5,800,475 A | 9/1998 | Jules |

(Continued)

FOREIGN PATENT DOCUMENTS

| | | |
|---|---|---|
| WO | WO 91/12783 | 9/1991 |
| WO | WO 99/07311 | 2/1999 |

(Continued)

OTHER PUBLICATIONS

International Search Report, for PCT/US2009/038890, dated May 29, 2009.
F.M. Vaneecloo et al., "Réhabilitation prothétique B.A.H.A des cophoses unilatérales", Annales D'oto-Laryngies et de Chirurgie Cervicofaciale, vol. 117, No. 6, Dec. 2000, pp. 410-417, 8 pages.
Michael Nolan et al., "Transcranial attenuation in bone conduction audiometry", The Journal of Laryngology and Otology, Jun. 1981, vol. 95, pp. 597-608, 12 pages.

(Continued)

*Primary Examiner* — Michael Carey
*Assistant Examiner* — Elizabeth K So
(74) *Attorney, Agent, or Firm* — Hauptman Ham, LLP; Martin J. Cosenza

(57) ABSTRACT

Methods and systems for fitting a bone conduction device are provided herein. These methods and systems comprise obtaining dynamic range parameters for a bone conduction device. These dynamic range parameters may include threshold and a maximum comfort levels for the bone conduction device. Once determined, the bone conduction device may use the dynamic range parameters in applying stimulation to a recipient.

27 Claims, 9 Drawing Sheets

(56) References Cited

U.S. PATENT DOCUMENTS

| | | | |
|---|---|---|---|
| 5,805,571 | A | 9/1998 | Zwan et al. |
| 5,825,894 | A * | 10/1998 | Shennib ............... A61B 5/121 381/17 |
| 5,913,815 | A | 6/1999 | Ball et al. |
| 6,602,202 | B2 | 8/2003 | John et al. |
| 6,643,378 | B2 | 11/2003 | Schumaier |
| 6,840,908 | B2 | 1/2005 | Edwards et al. |
| 7,018,342 | B2 | 3/2006 | Harrison et al. |
| 2002/0091423 | A1 * | 7/2002 | Rubinstein ............... A61B 5/12 607/55 |
| 2004/0064066 | A1 * | 4/2004 | John ................. A61B 5/04845 600/559 |
| 2004/0078057 | A1 | 4/2004 | Gibson |
| 2004/0082980 | A1 | 4/2004 | Mouine et al. |
| 2004/0204921 | A1 | 10/2004 | Bye et al. |
| 2005/0171579 | A1 | 8/2005 | Tasche et al. |
| 2006/0018488 | A1 | 1/2006 | Viala et al. |
| 2006/0287689 | A1 | 12/2006 | Debruyne et al. |
| 2008/0194984 | A1 * | 8/2008 | Keefe .......................... 600/559 |
| 2010/0041940 | A1 | 2/2010 | Hillbratt et al. |
| 2010/0222639 | A1 * | 9/2010 | Purcell ................ H04R 25/606 600/25 |
| 2011/0026721 | A1 | 2/2011 | Parker |
| 2011/0026748 | A1 | 2/2011 | Parker |

FOREIGN PATENT DOCUMENTS

| | | |
|---|---|---|
| WO | WO 2005/029915 | 3/2005 |
| WO | WO-2005122887 | 12/2005 |
| WO | WO 2007/140367 | 12/2007 |
| WO | WO 2009/124005 | 10/2009 |
| WO | WO 2009/124008 | 10/2009 |
| WO | WO 2009/124010 | 10/2009 |
| WO | WO 2010/017579 | 2/2010 |

OTHER PUBLICATIONS

European Patent Application No. 02 736 403.3, Office Communication dated Oct. 17, 2008. 6 Pages.
European Patent Application No. 02 736 403.3, Office Communication dated Apr. 27, 2009. 4 Pages.
European Patent Application No. 02 736 403.3, Office Communication dated Apr. 13, 2010. 6 Pages.
International Application No. PCT/SE02/01089, International Search Report dated Oct. 1, 2002. 3 Pages.
International Application No. PCT/SE02/01089, International Preliminary Examination Report dated Oct. 6, 2003. 5 Pages.
International Search Report issued by the International Searching Authority in connection with International Patent Application No. PCT/AU2009/001010, dated Nov. 25, 2009 (4 pages).
International Search Report issued by the International Searching Authority in connection with International Patent Application No. PCT/US2009/038879, dated May 22, 2009 (1 page).
Written Opinion issued by the International Searching Authority in connection with International Patent Application No. PCT/US2009/038879, dated May 22, 2009 (4 pages).
International Search Report issued by the International Searching Authority in connection with International Patent Application No. PCT/US2009/038884, dated Jun. 22, 2009.
Written Opinion issued by the International Searching Authority in connection with International Patent Application No. PCT/US2009/038884, dated Jun. 22, 2009 (5 pages).
Written Opinion issued by the International Searching Authority in connection with International Patent Application No. PCT/US2009/038890, dated May 29, 2009 (6 pages).
International Preliminary Report on Patentability issued by International Preliminary Examining Authority in connection with International Patent Application No. PCT/US2009/038890, dated Apr. 15, 2010 (8 pages).
Henry et al., "Bone Conduction: Anatomy, physiology, and Communication." Army Research Laboratory, Aberdeen Proving Ground, MD 21005-5425. May 2007 (206 pages).

* cited by examiner

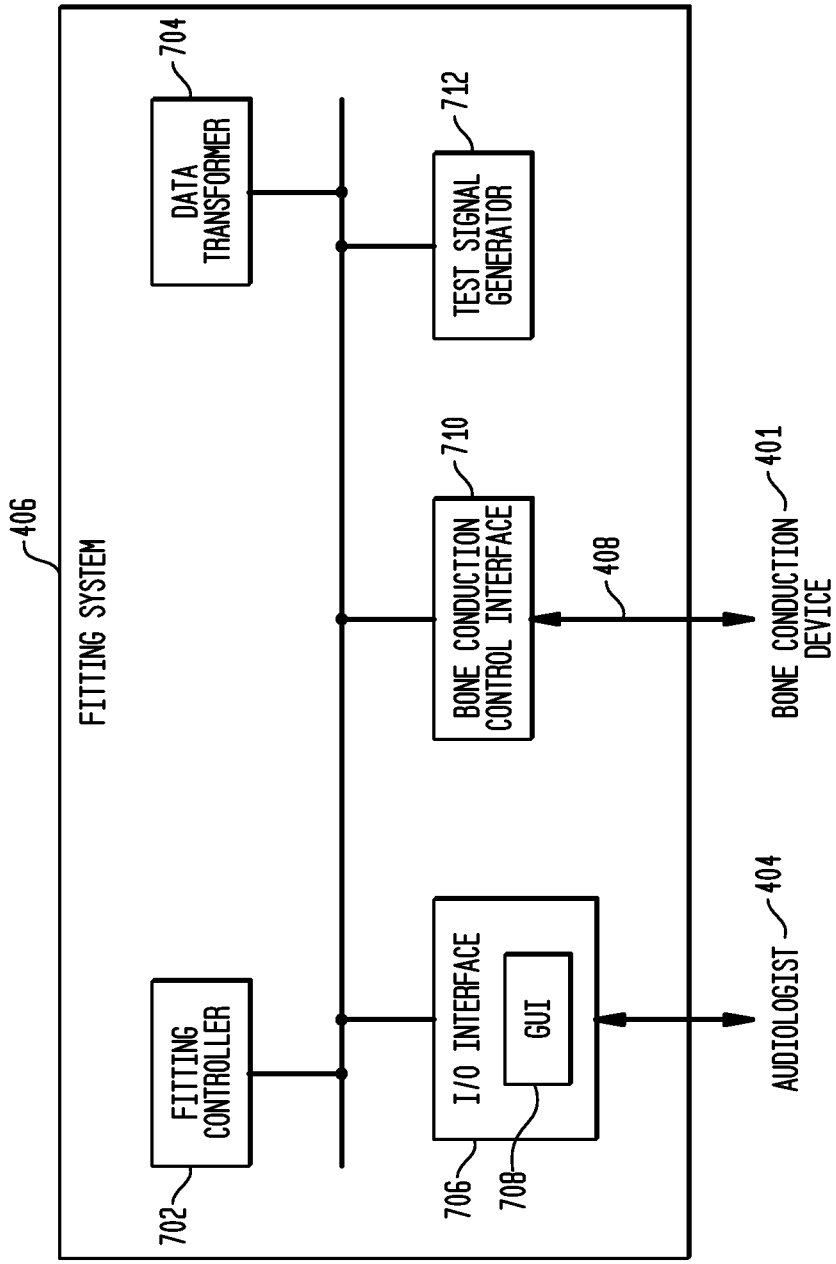

BONE CONDUCTION DEVICE FITTING

CROSS-REFERENCE TO RELATED APPLICATIONS

The present application is a National Stage Application of International Application No. PCT/US2009/38890, filed Mar. 31, 2009, and claims the benefit of U.S. Provisional Patent Application 61/041,185; filed Mar. 31, 2008. The contents of these applications are hereby incorporated by reference herein.

BACKGROUND

1. Field of the Invention

The present invention relates generally to bone conduction devices, and more particularly, to fitting a bone conduction device.

2. Related Art

Hearing loss, which may be due to many different causes, is generally of two types, conductive or sensorineural. In many people who are profoundly deaf, the reason for their deafness is sensorineural hearing loss. This type of hearing loss is due to the absence or destruction of the hair cells in the cochlea which transduce acoustic signals into nerve impulses. Various prosthetic hearing implants have been developed to provide individuals who suffer from sensorineural hearing loss with the ability to perceive sound. One such prosthetic hearing implant is referred to as a cochlear implant. Cochlear implants use an electrode array implanted in the cochlea of a recipient to provide electrical stimulation directly to the cochlea nerve, thereby causing a hearing sensation.

Conductive hearing loss occurs when the normal mechanical pathways that provide sound to hair cells in the cochlea are impeded, for example, by damage to the ossicular chain or ear canal. Individuals who suffer from conductive hearing loss may still have some form of residual hearing because the hair cells in the cochlea are generally undamaged.

Individuals who suffer from conductive hearing loss are typically not considered to be candidates for a cochlear implant due to the irreversible nature of the cochlear implant. Specifically, insertion of the electrode array into a recipient's cochlea results in the destruction of a majority of hair cells within the cochlea. This results in the loss of residual hearing by the recipient.

Rather, individuals suffering from conductive hearing loss typically receive an acoustic hearing aid. Hearing aids rely on principles of air conduction to transmit acoustic signals through the outer and middle ears to the cochlea. In particular, a hearing aid is typically positioned in the recipient's ear canal to amplify sound received at the outer ear of the recipient. This amplified sound reaches the cochlea and causes motion of the cochlear fluid and stimulation of the cochlea hair cells.

Unfortunately, not all individuals who suffer from conductive hearing loss are able to derive suitable benefit from hearing aids. For example, some individuals are prone to chronic inflammation or infection of the ear canal and cannot wear hearing aids. Other individuals have malformed or absent outer ear and/or ear canals as a result of a birth defect, or as a result of common medical conditions such as Treacher Collins syndrome or Microtia. Furthermore, hearing aids are typically unsuitable for individuals who suffer from single-sided deafness (total hearing loss only in one ear) or individuals who suffer from mixed hearing losses (i.e., combinations of sensorineural and conductive hearing loss).

When an individual having fully functioning hearing receives a sound, the sound is transmitted to the cochlea via two primary mechanisms: air conduction and bone conduction. As noted above, hearing aids rely primarily on the principles of air conduction. In contrast, other devices, referred to as bone conduction devices, rely predominantly on vibration of the bones of the recipients skull to provide acoustic signals to the cochlea.

Those individuals who cannot derive suitable benefit from hearing aids may benefit from bone conduction devices. Bone conduction devices convert a received sound into a mechanical vibration representative of the received sound. This vibration is then transferred to the bone structure of the skull, causing vibration of the recipient's skull. This skull vibration results in motion of the cochlear fluid. Hair cells inside the cochlea are responsive to this motion of the cochlea fluid, thereby generating nerve impulses, which result in the perception of the received sound.

SUMMARY

In one aspect of the invention a method is provided that comprises providing a test signal to a recipient of a bone conduction device; obtaining a response from the recipient to the provided test signal; determining a dynamic range parameter based on the obtained response; determining map data using the determined dynamic range parameter; and providing the map data to the bone conduction device for use by the bone conduction device in providing stimulation to the recipient.

In a second aspect, there is provided a fitting system for fitting a bone conduction device for a recipient. The fitting system comprises a user interface configured to provide data and receive input; a test signal generator configured to provide the recipient with a test signal generated in response to said control input, wherein the user interface is further configured to receive a response regarding the recipient's perception to the test signal; a controller configured to determine a dynamic range parameter based on the user response to the applied test signal, and further configured to determine map data for the bone conduction device using the determined dynamic range parameter; and an interface configured to provide the bone conduction device with the determined map data for use by the bone conduction device in providing stimulation to the recipient.

In a third aspect, there is provided a fitting system comprising means for providing a test signal to a recipient of a bone conduction device; means for obtaining a response from the recipient to the provided test signal; means for determining a dynamic range parameter based on the obtained response; means for determining map data using the determined dynamic range parameter; and means for providing the map data to the bone conduction device for use by the bone conduction device in providing stimulation to the recipient.

In a fourth aspect, there is provided a computer-readable media encoded with instructions operative to cause a computer to perform a method for at least partially fitting a medical implant system to a patient. This method comprises providing a test signal to a recipient of a bone conduction device; obtaining a response from the recipient to the provided test signal; determining a dynamic range parameter based on the obtained response; determining map data using the determined dynamic range parameter; and providing the map data to the bone conduction device for use by the bone conduction device in providing stimulation to the recipient.

In a fifth aspect, there is provided a method for use by a bone conduction device in providing stimulation. This method comprises receiving map data based on at least one dynamic range parameter measured for the bone conduction device; receiving a sound signal; and generating stimulation in response to the received acoustic sound signal using the received map data.

In a sixth aspect, there is provided bone conduction device comprising a sound input element configured to receive a sound signal; an interface configured to receive map data based on at least one dynamic range parameter measured for the bone conduction device; and a processor configured to generate stimulation in response to the received acoustic sound signal using the received map data.

In a seventh aspect, there is provided a bone conduction device comprising means for receiving map data based on at least one dynamic range parameter measured for the bone conduction device; means for receiving a sound signal; and means for generating stimulation in response to the received acoustic sound signal using the received map data.

BRIEF DESCRIPTION OF THE DRAWINGS

Embodiments of the present invention are described herein in conjunction with the accompanying drawings, in which:

FIG. 7 is a high-level functional block diagram of a fitting system, in accordance with embodiments of the present invention;

DETAILED DESCRIPTION

Aspects of the present invention are generally directed to obtaining dynamic range parameters for a bone conduction device. Dynamic range parameters may include threshold and maximum comfort levels for the recipient of the bone conduction device. Once determined, the bone conduction device may use the dynamic range parameters in applying stimulation to a recipient.

Figure 1:
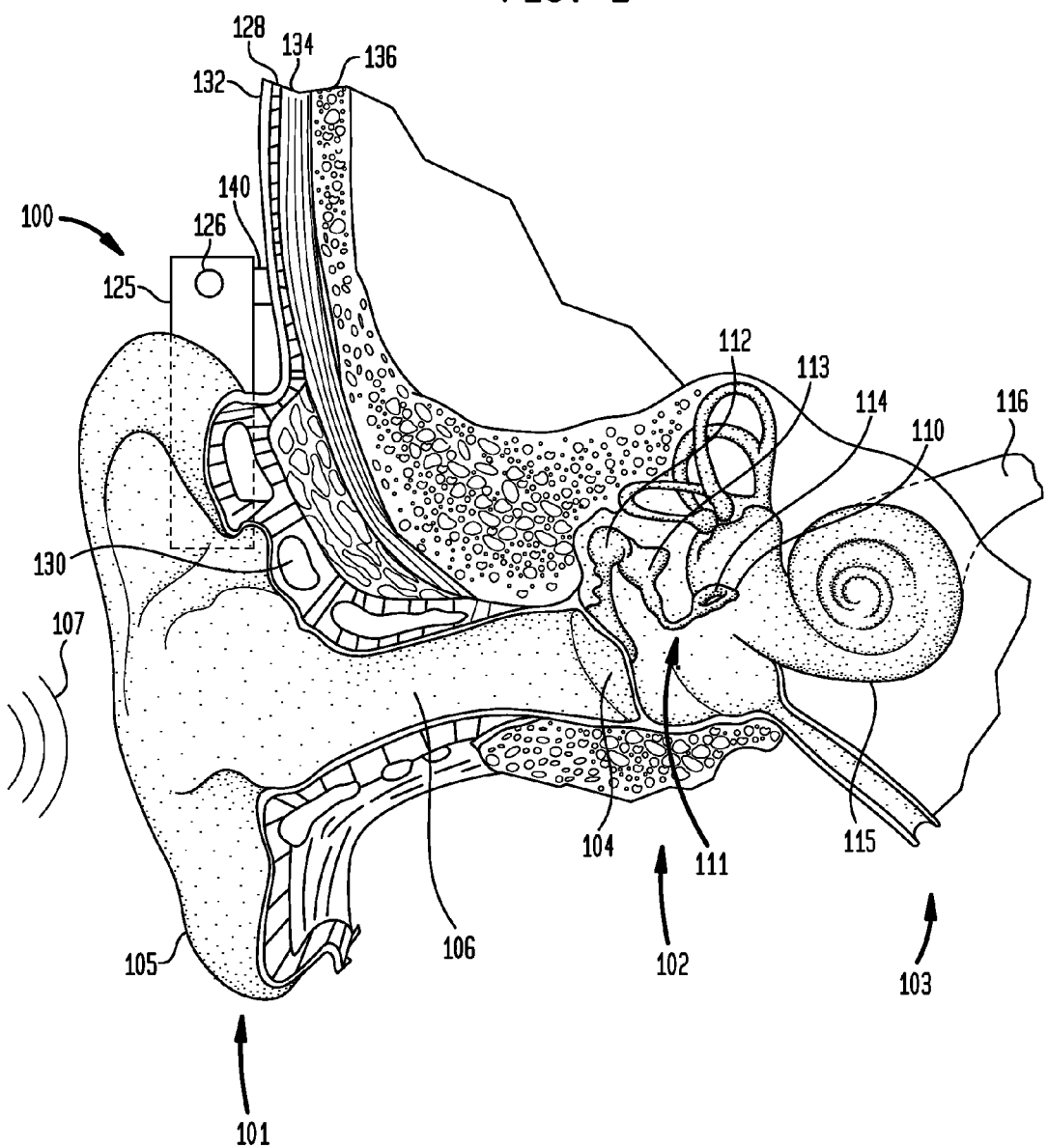
FIG. 1 is a perspective view of a bone conduction device, in which embodiments of the present invention may be advantageously implemented.

FIG. 1 is a cross sectional view of a human ear and surrounding area, along with a side view of one of the embodiments of a bone conduction device 100. In fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. The motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 may be positioned behind outer ear 101 of the recipient; however it is noted that device 100 may be positioned in any suitable manner.

In the embodiments illustrated in FIG. 1, bone conduction device 100 comprises a housing 125 having at least one microphone 126 positioned therein or thereon. Housing 125 is coupled to the body of the recipient via coupling 140. As described below, bone conduction device 100 may comprise a signal processor, a transducer, transducer drive components and/or various other electronic circuits/devices.

In accordance with embodiments of the present invention, an anchor system (not shown) may be implanted in the recipient. As described below, the anchor system may be fixed to bone 136. In various embodiments, the anchor system may be implanted under skin 132 within muscle 134 and/or fat 128 or the hearing device may be anchored in another suitable manner. In certain embodiments, a coupling 140 attaches device 100 to the anchor system.

Figure 2A:
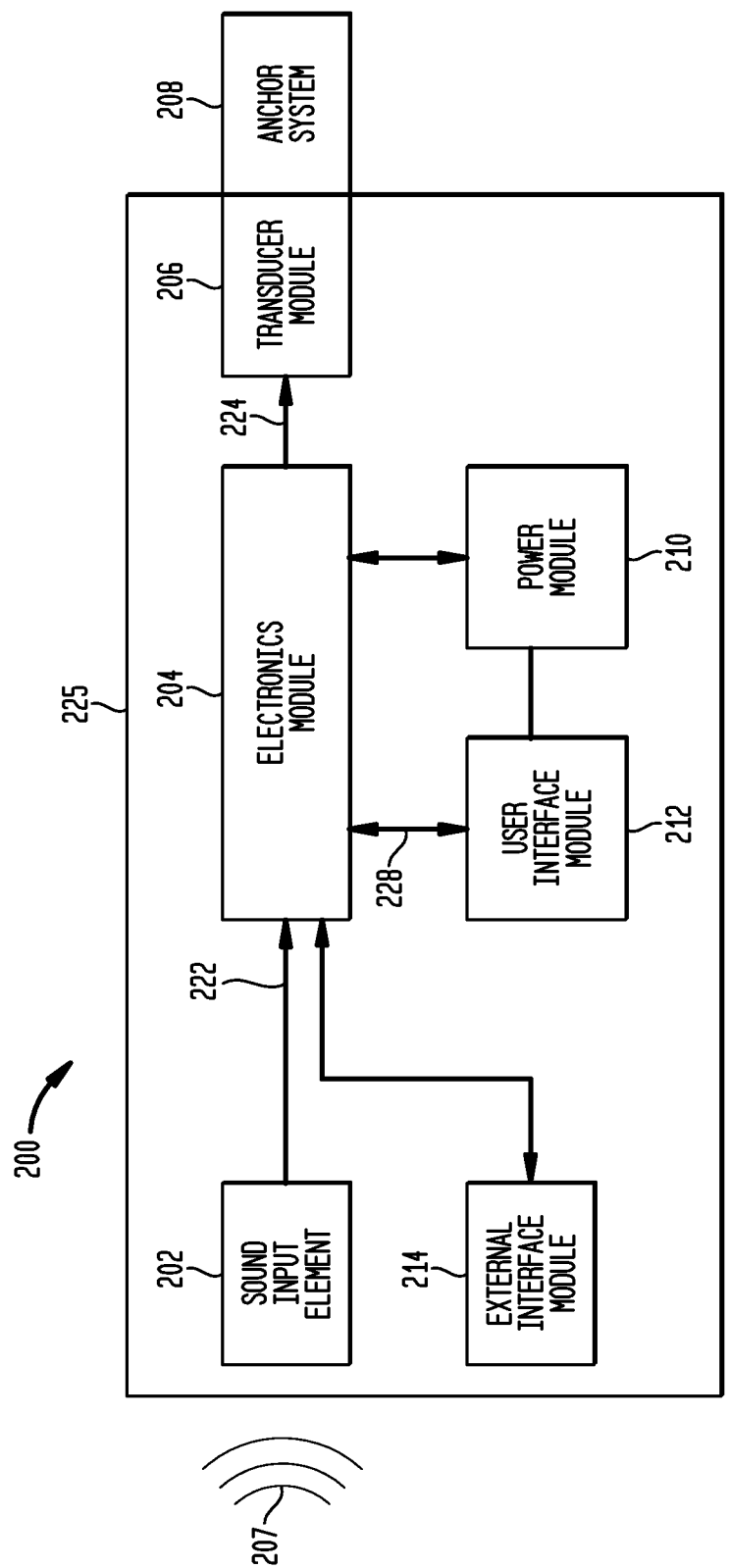
FIG. 2A is a high-level functional block diagram of a bone conduction device, such as the bone conduction device of FIG. 1, in accordance with embodiments of the present invention.

A functional block diagram of one embodiment of bone conduction 100, referred to as bone conduction device 200, is shown in FIG. 2A. In the illustrated embodiment, a sound 207 is received by a sound input element 202. In some embodiments, sound input element 202 is a microphone configured to receive sound 207, and to convert sound 207 into an electrical signal 222. As described below, in other embodiments sound 207 may received by sound input element 202 as an electrical signal.

As shown in FIG. 2A, electrical signal 222 is output by sound input element 202 to an electronics module 204. Electronics module 204 is configured to convert electrical signal 222 into an adjusted electrical signal 224. As described below in more detail, electronics module 204 may include a sound processor, control electronics, transducer drive components, and a variety of other elements.

As shown in FIG. 2A, a transducer 206 receives adjusted electrical signal 224 and generates a mechanical output force that is delivered to the skull of the recipient via an anchor system 208 coupled to bone conduction device 200. Delivery of this output force causes one or more of motion or vibration of the recipient's skull, thereby activating the hair cells in the cochlea via cochlea fluid motion.

FIG. 2A also illustrates a power module 210. Power module 210 provides electrical power to one or more components of bone conduction device 200. For ease of illustration, power module 210 has been shown connected only to user interface module 212 and electronics module 204. However, it should be appreciated that power module 210 may be used to supply power to any electrically powered circuits/components of bone conduction device 200.

Bone conduction device 200 further includes a user interface module 212 that allows the recipient to interact with device 200. For example, user interface module 212 may allow the recipient to adjust the volume, alter the speech processing strategies, power on/off the device, etc. User interface module 212 communicates with electronics module 204 via signal line 228.

Bone conduction device 200 may further include an external interface module 214 that may be used to connect electronics module 204 to an external device, such as a fitting system. Using external interface module 214, the external device, may obtain information from the bone conduction device (e.g., the current parameters, data, alarms, etc.) and/or modify the parameters of the bone conduction device 200 used in processing received sounds.

In the embodiment illustrated in FIG. 2A, sound input element 202, electronics module 204, transducer 206, power module 210, user interface module 212, and external interface module 214 been shown as integrated in a single housing, referred to as housing 225. However, it should be appreciated that in certain embodiments of the present invention, one or more of the illustrated components may be housed in separate or different housings. Similarly, it should also be appreciated that in such embodiments, direct connections between the various modules and devices are not necessary and that the components may communicate, for example, via wireless connections.

Figure 2B:
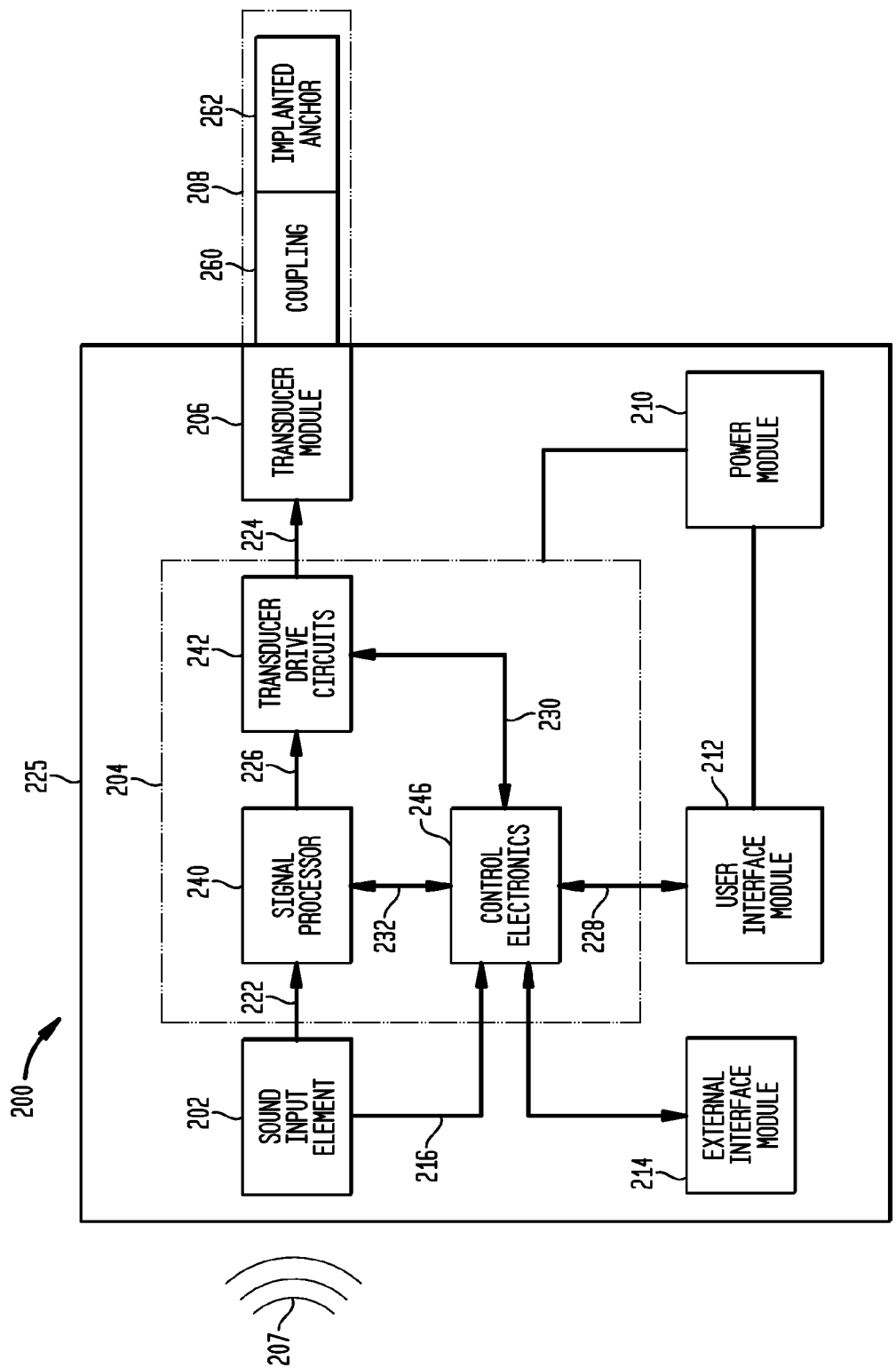
FIG. 2B is detailed functional block diagram of the bone conduction device illustrated in FIG. 2A, in accordance with embodiments of the present invention.

FIG. 2B provides a more detailed view of bone conduction device 200 of FIG. 2A. In the illustrated embodiment, electronics module 204 comprises a sound processor 240, transducer drive components 242 and control electronics 246. As explained above, in certain embodiments sound input element 202 comprises a microphone configured to convert a received acoustic signal into electrical signal 222. In other embodiments, as detailed below, sound input element 202 receives sound 207 as an electrical signal.

In embodiments of the present invention, electrical signal 222 is output from sound input element 202 to sound processor 240. Sound processor 240 uses one or more of a plurality of techniques to selectively process, amplify and/or filter electrical signal 222 to generate a processed signal 224A. In certain embodiments, sound processor 240 may comprise substantially the same sound processor as is used in an air conduction hearing aid. In further embodiments, sound processor 240 comprises a digital signal processor.

Processed signal 226A is provided to transducer drive components 242. Transducer drive components 242 output a drive signal 224B, to transducer 206. Based on drive signal 224B, transducer 206 provides the output force to the skull of the recipient. For ease of description, the electrical signal supplied by transducer drive components 242 to transducer 206 has been referred to as drive signal 224B. However, it should be appreciated that processed signal 224B may comprise an unmodified version of processed signal 224A.

As noted above, transducer 206 generates an output force to the skull of the recipient via anchor system 208. As shown in FIG. 2B, anchor system 208 comprises a coupling 260 and an implanted anchor 262. Coupling 260 may be attached to one or more of transducer 206 or housing 225. For example, in certain embodiments, coupling 260 is attached to transducer 206 and vibration is applied directly thereto. In other embodiments, coupling 260 is attached to housing 225 and vibration is applied from transducer 206 through housing 225.

As shown in FIG. 2B, coupling 260 is coupled to an anchor implanted in the recipient, referred to as implanted anchor 262. As explained with reference to FIG. 3, implanted anchor 262 provides an element that transfers the vibration from coupling 260 to the skull of the recipient.

As shown, control electronics 246 may be connected to one or more of user interface module 212, external interface module 214, sound input element 202, sound processor 240 and/or transducer drive components 242. In embodiments, based on inputs received at user interface module 212 or external interface module 214, control electronics 246 may provide instructions to, or request information from, other components of bone conduction device 200.

As noted above, a recipient may control various functions of the device via user interface module 212. User interface module 212 includes one or more components that allow the recipient to provide inputs to, or receive information from, elements of bone conduction device 200. Further, as noted above, external interface module 214 may be used to connect electronics module 204 to an external device, such as a fitting system. Using external interface module 214, a fitting system may be able to obtain and/or modify information for the various components of bone conduction device 200. For example, in an embodiment, a fitting system may use external interface module 214 to obtain and modify the parameters of sound processor 240 used in processing, amplifying, and filtering the received sound. External interface module 214 may comprise a plug for permitting a wired connection between bone conduction device and an external device, or, for example, wireless communications hardware and/or software to permit a wireless connection between bone conduction device and an external device. Such a wireless connection may use any appropriate wireless mechanism, such as, for example, Wi-Fi (IEEE 802.11), Bluetooth, etc.

Figure 3:
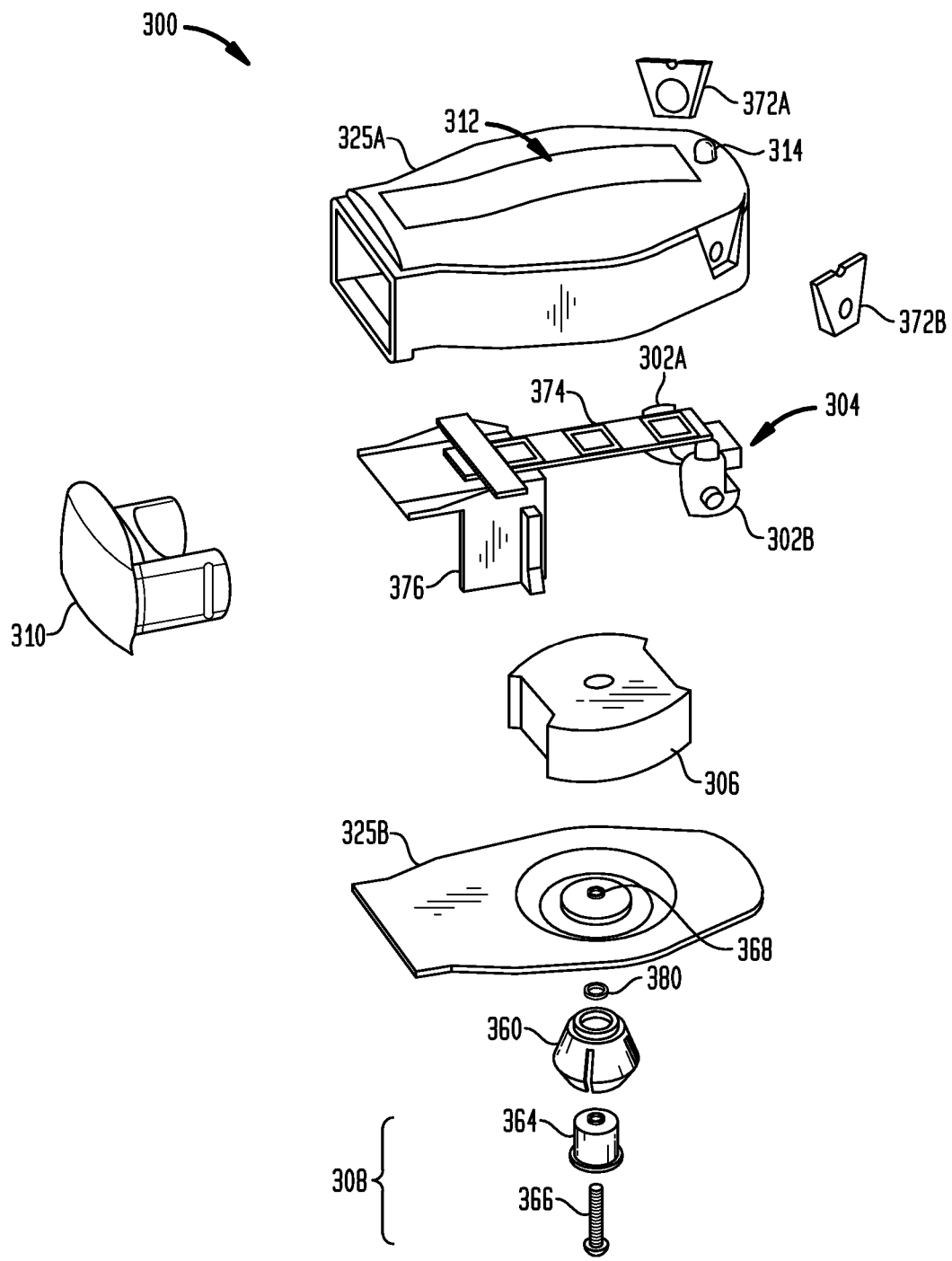
FIG. 3 is an exploded view of the bone conduction device illustrated in FIG. 1, in accordance with embodiments of the present invention.

FIG. 3 illustrates an exploded view of one embodiment of bone conduction 200 of FIGS. 2A and 2B, referred to herein as bone conduction device 300. As shown, bone conduction device 300 comprises an embodiment of electronics module 204, referred to as electronics module 304. As explained above, electronics module 304 may include a sound processor, transducer drive components and control electronics. These components may be separate components or included in a single component (e.g., a microprocessor, application specific integrated circuit (ASIC), etc.).

In the illustrated embodiment, electronics module 304 includes a printed circuit board 374 (PCB) to electrically connect and mechanically support the components of electronics module 304. Attached to PCB 374 are one or more sound input elements, shown as microphones 302 to receive a sound.

In the illustrated embodiment, bone conduction device 300 further comprises battery shoe 310 for supplying power to components of device 300. Battery shoe 310 may include one or more batteries. In certain embodiments, PCB 374 is attached to a connector 376. Connector 376 is configured to mate with battery shoe 310. In certain embodiments, connector 376 and battery shoe 310 may be releasably snap-locked to one another. Furthermore, in such embodiments, one or more battery connects (not shown) are disposed in connector 376 to electrically connect battery shoe 310 with electronics module 304.

In the embodiment illustrated in FIG. 3, bone conduction device 300 further includes a two-part housing 325, comprising first housing portion 325A and second housing portion 325B. Housing portions 325 are configured to mate with one another to substantially seal bone conduction device 300.

In the embodiment of FIG. 3, first housing portion 325A has an opening therein for receiving battery shoe 310. In such embodiments, battery shoe protrudes through first housing portion 325A and may be removed or inserted by the recipient. Also in the illustrated embodiment, microphone covers 372 are releasably attached to first housing portion 325A. Microphone covers 372 provide a barrier over microphones 302 to protect microphones 302 from dust, dirt or other debris.

Bone conduction device 300 further includes an embodiment of user interface module 212, referred to herein as user interface module 312. User interface module 312 is configured to provide or receive user inputs from the recipient.

Also as shown in FIG. 3, bone conduction device 300 comprises an embodiment of transducer 206, referred to as transducer 306. Transducer 306 generates an output force that causes movement of the cochlea fluid so that a sound may be perceived by the recipient. The output force may result in mechanical vibration of the recipient's skull, or in physical movement of the skull about the neck of the recipient. As noted above, in certain embodiments, bone conduction device 300 delivers the output force to the skull of the recipient via an anchor system 308. Anchor system 308 comprises a coupling 360 and implanted anchor 362. In the embodiment illustrated in FIG. 3, coupling 360 is configured to be attached to second housing portion 325B. As such, in this embodiment, vibration from transducer 306 is provided to coupling 360 through housing 325B. In the embodiment shown in FIG. 3, an opening 368 is provided in second housing portion 325B. A screw (not shown) may be inserted through opening 368 to attach transducer 306 to coupling 360. In such embodiments, an O-ring 380 may be provided to seal opening 368 around the screw.

As noted above, anchor system 308 includes implanted anchor 362. Implanted anchor 362 comprises a bone screw 366 implanted in the skull of the recipient and an abutment 364. In an implanted configuration, screw 366 protrudes from the recipient's skull through the skin. Abutment 364 is attached to screw 366 above the recipient's skin. In other embodiments, abutment 364 and screw 366 may be integrated into a single implantable component. Coupling 360 is configured to be releasably attached to abutment 364 to create a vibratory pathway between transducer 306 and the skull of the recipient.

Bone conduction device 300 further includes an embodiment of external interface module 214, referred to herein as external interface module 314. External interface module 314 may include a jack connector for receiving a plug for a wired connection to an external device. Or, for example, external interface module 314 may comprise hardware and/or software for wirelessly connecting to an external device.

In alternative embodiments of the present invention, bone conduction device 300 may comprise one or more additional sound input elements. For example, bone conduction device 300 may comprise an electrical input 316. In such embodiments, the electrical input is configured to connect device 300 to external equipment and receive an electrical sound signal directly therefrom. Electrical input 316 may permit bone conduction device 300 to be connected to, for example, FM hearing systems, MP3 players, televisions, mobile phones, etc.

In still other embodiments, a further sound input element in the form of a telecoil 318 may be integrated in, or connected to, bone conduction device 300. Telecoil 318 permits bone conduction device 300 to receive input signals from, for example, a telephone or other similar device.

Figure 4:
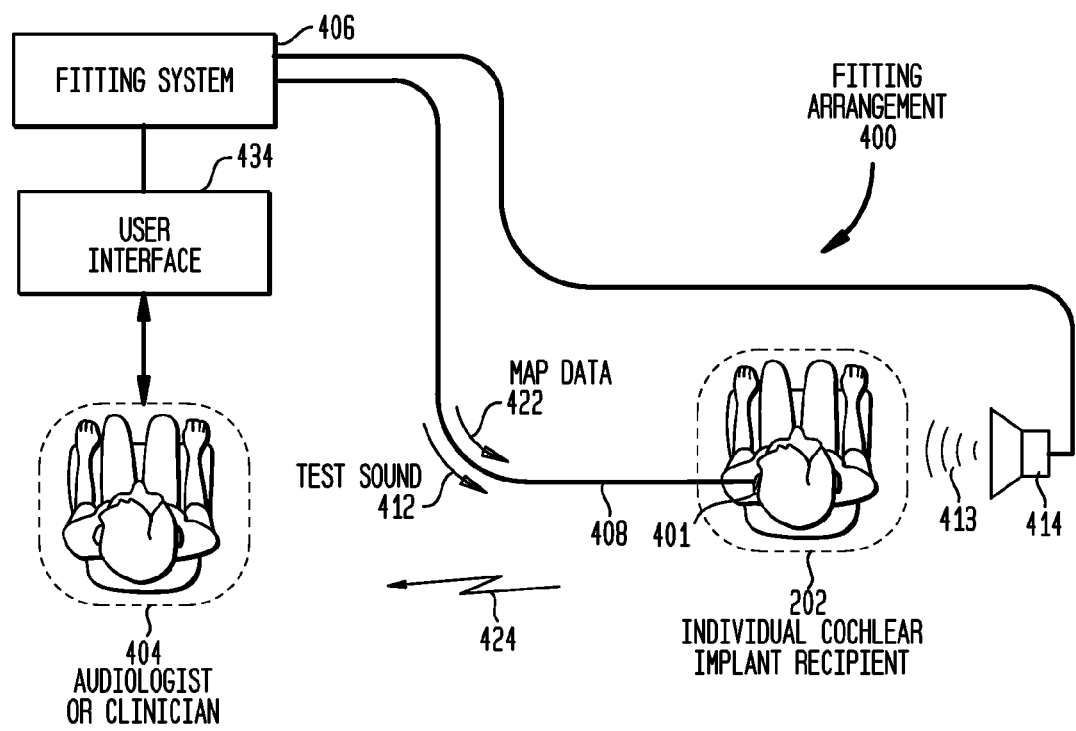
FIG. 4 is a schematic diagram illustrating one exemplary arrangement in which a fitting system may be implemented for use in determining the bone conduction device's dynamic range, in accordance with embodiments of the present invention.
Figure 5:
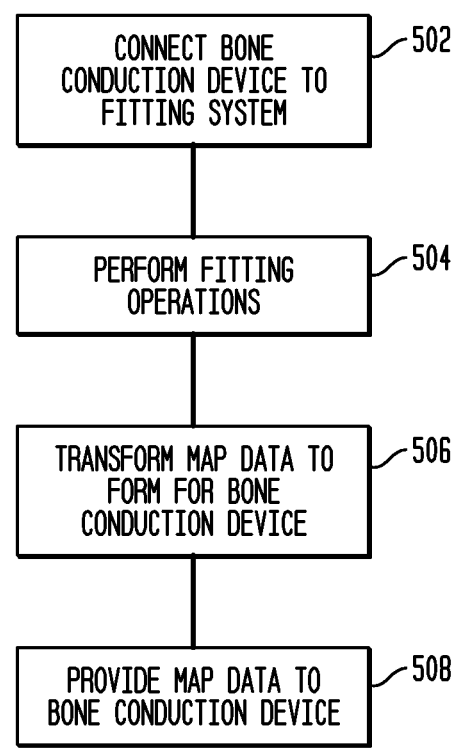
FIG. 5 is a high-level flow chart illustrating operations that may be performed while fitting a bone conduction device, in accordance with embodiments of the present invention.

As noted above, in embodiments, a dynamic range of the bone conduction device may determined and this dynamic range used in processing the acoustic signals. FIG. 4 is a schematic diagram illustrating of an exemplary arrangement 400 in which a fitting system 406 may be implemented for use in fitting a bone conduction device 401. As will be discussed in more detail below, fitting arrangement 400, in fitting conbed conduction device 401, may determine the bone conduction device's dynamic range. This dynamic range may be defined in terms of one or more dynamic parameters, such as a threshold level and a maximum comfortable loudness level (referred to herein simply as "comfort level") for the bone conduction device. Threshold levels are comparable to acoustic threshold levels; comfort levels indicate the level at which a sound is loud but comfortable. FIG. 5 is a high-level flow chart illustrating operations that may be performed while fitting bone conduction device 100 utilizing the fitting system illustrated in FIG. 4 to measure dynamic range parameters for a bone conduction device.

An audiologist 404 may use fitting system 406 to create individualized recipient MAP data 422 that is to be used for subsequent operations by bone conduction device 401. This MAP data 422 may comprise individualized programs, commands, data, settings, parameters, instructions, and/or other information (generally and collectively referred to as a "MAP data" herein) that define the specific characteristics used by the bone conduction device 401 in applying stimulation to the recipient 402. After determining the MAP data, fitting system 406 may digitally store the MAP data on system 406 and ultimately download the MAP data 422 to the memory of electronics module 204 of bone conduction device 401.

In certain embodiments, fitting system 406 comprises computer hardware and software, including, for example, one or more interfaces for connecting to a speaker 414, bone conduction device 401, a display device (e.g., monitor), and a user input device(s) (e.g., keyboard, mouse, touchscreen, etc.). For explanatory purposes, audiologist 404 will hereinafter to refer to any person operating fitting system 406 whether an audiologist, clinician, or any other person.

User interface 334 may comprise any device which may be used by audiologist 404 to communicate with fitting system 206. For example, user interface 334 may comprise a display device for displaying information from fitting system 406 to audiologist 404. Exemplary display devices include, for example, a computer monitor, touch screen device, etc. Additionally, user interface 334 may comprise one or more input devices for enabling audiologist 402 to provide information, such as instructions or data, to fitting system 206. Exemplary input devices include a computer keyboard, mouse, voice-responsive software, touch-screen, retinal control, joystick, and any other data entry or data presentation formats now or later developed.

In the embodiment illustrated in FIG. 4, bone conduction device 401 may be connected directly to fitting system 406 to establish a data communication link 408 between the bone conduction device 401 and fitting system 406 at block 502. System 406 is thereafter bi-directionally coupled by means of data communication link 408 with bone conduction device 401. It should be appreciated that although bone conduction device 401 and fitting system 406 are connected via a cable in FIG. 4, any communications link now or later developed may be utilized to communicably couple the implant and fitting system, such as, for example, a wireless communications link.

After connecting fitting system 406 and bone conduction device 401, an audiologist may use the fitting system to perform fitting operations at block 504. As used herein, fitting of bone conduction device 401 (also commonly referred to as "programming" or "mapping") refers to creating a set of instructions (data or code; "mapping data" 422 herein) that define the specific characteristics used in processing received acoustic signals. Referring back to FIG. 2, this processing may be performed by signal processor 240 of bone conduction device 200. This set of instructions may be referred to as the bone conduction device's "program" or "map."

In certain embodiments, this MAP data may comprise instructions for applying a gain to a received acoustic signal, a transfer function for amplifying the received acoustic signals, the measured dynamic parameters, and/or the current level(s) for transducer drive circuits 224 to apply such that correspondingly applied vibration falls within the measured dynamic range of the device. An exemplary method for performing fitting operations at block 504 will be discussed in further detail below with reference to FIG. 6.

At block 508 of FIG. 5, fitting system 406 transforms the MAP data from the fitting system's domain to the domain of bone conduction device 501. The MAP data 422 is downloaded from fitting system 406 to bone conduction device 401 at block 510. The bone conduction device 401 may then use the provided MAP data in applying stimulation. As a result, in embodiments in which acoustic stimulation is provided, from the audiologist's point of view, this fitting process may be similar to the fitting of conventional hearing aids, wherein an audiologist measures hearing threshold and comfort levels across the audible frequency range (e.g., 20 Hz-20 kHz) using acoustic stimuli.

Figure 6:
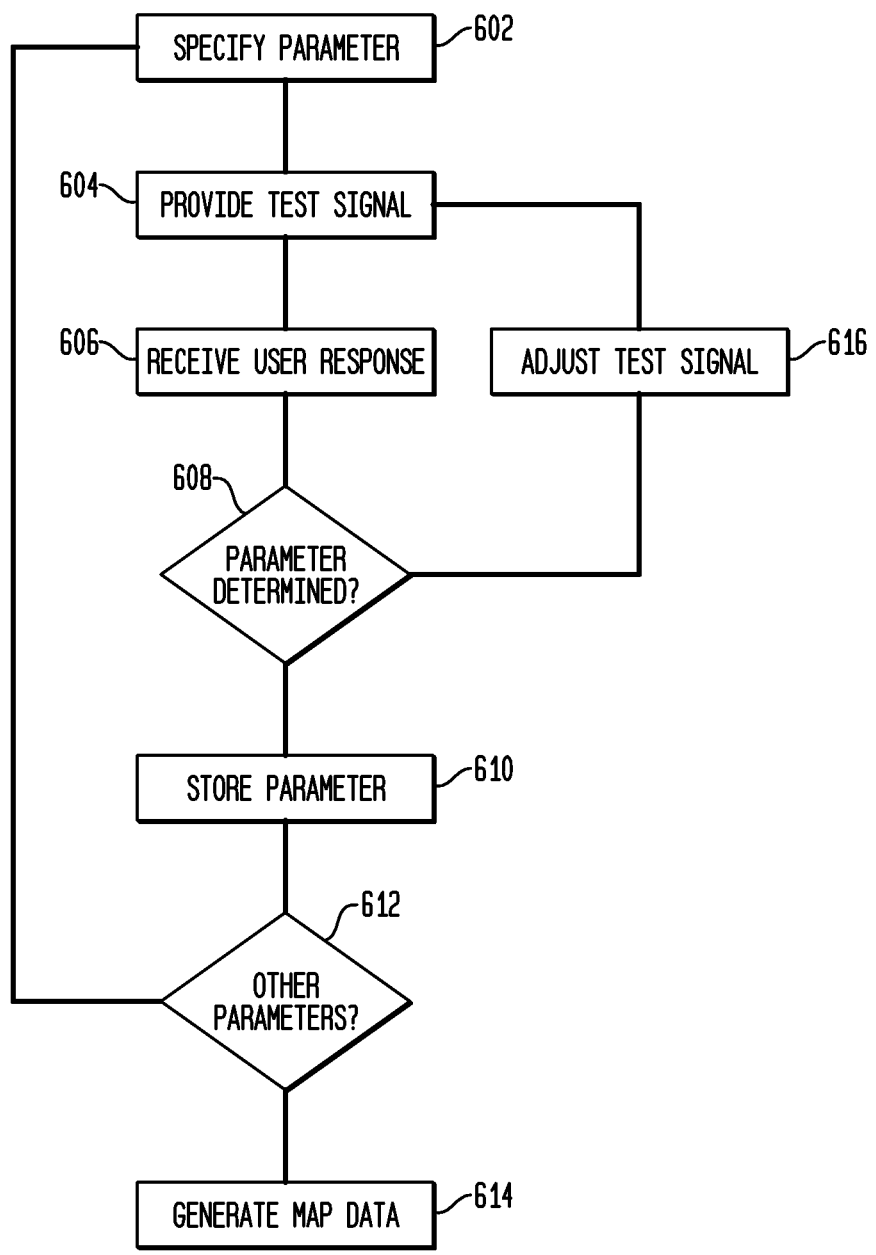
FIG. 6 is a flow chart of the fitting operations which may be performed, in accordance with embodiments of the present invention.

FIG. 6 provides an exemplary method for performing fitting operations, in accordance with an embodiment of the present invention. FIG. 6 will be described with reference to FIGS. 2 and 4. In this exemplary method, fitting system 406 provides the audiologist with a user interface that provides and receives acoustic-based data; that is, data which is in the form commonly used by audiologists to fit hearing aids. Such data may be presented as one or more graphs or plots illustrating frequency-gain relationships, although other presentations are feasible. These graphs or plots may, for example, be displayed on a display device (e.g., computer monitory) of fitting system 406.

At block 602, audiologist 404 specifies the dynamic range parameter to be measured. As noted above, exemplary dynamic range parameters include threshold and comfort levels for bone conduction device 401. In some embodiments, fitting system 406 may be used to measure the threshold and comfort levels for bone conduction device 401 for each of set of frequencies encompassing the frequency range of the bone conduction device 401 (e.g., 20 Hz to 20 kHz, 125-8000 Hz), such as, for example, if bone conduction device 401 has a narrower frequency range. The frequencies for which levels are measured may be, for example, specified in a logarithmic fashion. For example, if the frequency range of 20 Hz to 20 kHz is used, the frequencies for which levels are obtained may include frequencies every 10 Hz between 20 Hz and 100 Hz (20, 30, 40 . . . , 90, 100), every 100 Hz between 100 Hz and 1 kHz (100, 200, . . . , 900, 1000), every 1 kHz between 1 kHz and 10 kHz (1000, 2000, . . . 9000, 10000), and at 20 kHz. Levels for frequencies between these measured values may be interpolated by, for example, fitting a curve to the measured values. It should be noted that this is just one example for specifying frequencies for threshold and/or comfort level measurement, and others may be used without departing from the invention. For example, in another embodiment, fitting system 406 may obtain only the levels for a much smaller subset (e.g., 5 frequencies spaced over the frequency range) and the remaining frequencies determined by fitting a curve to the measured values. This fitted curve may match, for example, curves found for other recipients, a population of recipients sharing similar characteristics with the recipient 402, a default curve, etc. Or, in another example, bone conduction device 401 may split its frequency range into separate frequency bands, and use fitting system 406 to measure the threshold and/or comfort level for each of these bands. Additionally, audiologist 404 may use the user interface to specify or adjust the frequencies for which fitting system 406 measures the dynamic range parameters (e.g., threshold and/or comfort levels).

After specifying the dynamic parameter to be measured, audiologist 404 may direct fitting system 406, using the user interface, to apply stimulation at the frequency or frequencies corresponding to the selected parameter at block 604. In response, fitting system 406 may send a signal to bone conduction device 401 to instruct transducer module 205 to cause a vibration at the specified frequency. Initially, the intensity of this vibration may be below the expected level for the recipient. For example, if the dynamic parameter to be measured is the threshold level for a particular frequency, fitting system 406 may initially direct that the intensity of the stimulation be very low. Fitting system 406 may use various techniques to apply this stimulation. For example, in one embodiment, fitting system 406 may send an instruction to the sound processor of bone conduction device 401 to produce a vibration at a particular frequency and with a particular intensity as measured in, for example, the current level used by the transducer to provide the stimulation. Or, for example, fitting system 406 may send an acoustic signal to bone conduction device 401 at a particular frequency and at a particular intensity, as measured in terms of decibels (dB), that the bone conduction device 401 may process to provide the stimulation.

After application of the stimulation, the audiologist 404 may obtain a response from the recipient 402 at block 606. As noted above, this verbal feedback from the recipient may indicate the recipient's perception of the applied stimulation. For example, in the case of measuring a threshold level, this verbal feedback may include the recipient 402 stating whether or not they heard the applied stimulation. Or, for example, in the case of measuring a comfort level, the verbal feedback may include the recipient 402 stating whether or not that sound heard is at a comfortable level or not. The audiologist 404 may then, for example, provide the recipient's response to fitting system 406 via the user interface.

The audiologist 404 may then determine whether the parameter has been determined or not at block 608. If determined, the audiologist 404 may instruct fitting system 406 that the parameter has been determined via the user interface and, in response, fitting system 406 may store the determined parameter at block 610. Next, fitting system 406 may ask the audiologist via the user interface if additional parameters are to be measured at block 612. If so, the process may return to block 602 and another parameter may be selected. If not, the process may proceed to block 614 where fitting system 406 generates MAP data using the measured dynamic range parameters.

If at block 606, the audiologist 404 determines that the parameter has not yet been determined, fitting system 406 may adjust the intensity of the test signal at block 616. The process may then return to block 604, and the test signal applied at this new intensity. In adjusting the intensity of the test signal at block 616, fitting system 406 may use different techniques depending on the type of dynamic range parameter being measured. For example, threshold levels may be obtained using an ascending presentation, followed by a bracketing procedure; and, comfort levels may be obtained through a method referred to as loudness scaling. These procedures for obtaining threshold and comfort levels may be similar to the procedures commonly used in obtaining threshold and comfort levels for cochlear implants or hearing aid. For example, while measuring a threshold level, the audiologist 404 may instruct fitting system 406 at block 616 to gradually increase the intensity of the vibration until the recipient 402 provides an indication (e.g., verbally, or in the case of small children in some other manner) that they perceive a sound in response to the applied stimulation. As noted above, the threshold, in this example, is a psychophysical judgment of loudness and corresponds to the minimum intensity at which sound at the frequency is perceived by the recipient. The measured threshold level may then be stored by fitting system 406 for later use in determining and providing the MAP to bone conduction device 401. Or, for example, in the case of measuring a comfort level, the audiologist 404 may direct fitting system 406 at block 616 to gradually increase the intensity of the vibration until the recipient 402 indicates (e.g., verbally or in some other manner) that the vibration is no longer comfortable. The audiologist 404 may then direct fitting system 406 to decrease the intensity at block 616 until the intensity is comfortable for the recipient 402. The measured and stored threshold and/or comfort levels may be, for example, in terms of the current level for the intensity of the applied stimulation. Or, for example, if the test signal is an acoustic signal, the threshold and/or comfort levels may be stored in terms of sound pressure level (e.g., dB).

In some implementations, the bone conduction device 401 may never reach an intensity that is uncomfortable to the recipient. In such cases, the maximum intensity that may be applied by the bone conduction device 401 may be stored as the comfort level for the specified frequency. In other embodiments, the comfort levels may not be measured, but instead may be calculated from the measured thresholds, or, for example, set to the maximum intensity that may be provided by the bone conduction device.

As noted above, fitting system 406 may generate MAP data for the bone conduction device 401 using the measured dynamic range parameters at block 614. In an embodiment, fitting system 406 only measures the dynamic range parameter(s) for a particular number of specific frequencies. The dynamic range parameter(s) (e.g., threshold and comfort levels) for frequencies other than the specified frequencies may be calculated from the measured levels by fitting a curve to these measured levels. This MAP data (e.g., the curves) may then be displayed to the audiologist 404 by fitting system 406 on a display device of fitting system. The audiologist 404 using the user interface of fitting system 406 may then adjust the levels, for example, by adjusting the curves as a whole, or by adjusting individual levels. The audiologist 404 may then save the final levels and direct fitting system 406 to determine the MAP data at block 614 using these final levels. This MAP data may be in various forms depending on the specifics of the bone conduction device. For example, this MAP data may include a data table (e.g., specifying the threshold and/or comfort levels to be used by the bone conduction device), the curves, a transfer function for use by the bone conduction device, etc. A further description of exemplary MAP data is provided below.

FIG. 7 is a high-level functional block diagram of a fitting system 406 according to an embodiment. The primary components and operative aspects of fitting system 406 are shown in block diagram form for ease of description, and are described herein. As illustrated, the components may be coupled by a communications bus. However, it is to be understood that the components of fitting system 406 may be connected in any manner suitable for the particular application. Additionally, these components may be software functions executed by a processor. It should be noted that these functions are illustrated as separate functional blocks for explanatory purposes, and in implementation the functions may be combined in other manners.

As illustrated, fitting system 406 may comprise a fitting controller 702, a data transformer 404, a user interface 406, a bone conduction control interface 710, and a test signal generator 712. Fitting controller 702 may control the other components of fitting system 406 and control the operations of the fitting process. Bone conduction control interface 710 may be used to send information, such as MAP data 422 and instructions, to bone conduction device 401 via data communication link 408.

Test signal generator 712 may generate test signal 412. As discussed above, test signal 412 may comprise an instruction for bone conduction device 401 to generate stimulation at a particular intensity level. In such an embodiment, the test signal may be sent to bone conduction device 401 via bone conduction device control interface 710. Or, for example, test signal 412 may comprise an acoustic signal such as a pure tone, a plurality of tones, etc. In such embodiments, test signal generator 712 may be connected (e.g., via the fitting system's bus) to a sound interface (not shown) that may be used to connect one or more speakers, headphones, or other sound generating devices to produce acoustic sounds generated by test signal generator 712.

Input/output interface 706 may comprise, for example, any type interface or interfaces that may be used for connecting a user interface 434. As noted above, user interface 434 may comprise, for example, a display device, a computer keyboard, mouse, voice-responsive software, touchscreen, retinal control, joystick, and any other data entry or data presentation formats now or later developed, or an interface for connecting to any such device. Input/output interface 706 may also comprise an interface for connecting to a display device, such as a computer monitor, television, etc. Input/output interface 706 may also be capable of receiving input from the audiologist 404 using a graphical user interface (GUI) 708 which may be displayed on a display device, as noted above. As noted, input/output interface 706 may provide and receive acoustic-based data;

that is, data which is in the form commonly used by audiologists to fit hearing aids. In an embodiment, such data may be presented as frequency-gain data displays.

Data transformer 704 may transform fitting system 406 based MAP data to implant-based MAP data 422. The mechanisms employed by data transformer 704 may depend on the units in which the dynamic range data was determined as well as the particular bone conduction device 401. As noted above, in an embodiment, thresholds and comfort levels may be determined in terms of current levels for use by the transducer in providing stimulation. In such an embodiment, data transformer 704 may simply provide these current levels to bone conduction device 401.

Or, for example, data transformer 704 may convert the received threshold levels to a gain curve for use by the bone conduction device 401. In such an embodiment, fitting system 406 may store information regarding default sound pressure levels, such as, for example, the sound pressure levels for the threshold levels for a person of normal hearing. Using these default sound pressure levels, data transformer 704 may generate a gain curve. This gain curve may comprise the gain per frequency that bone conduction device 401 is to apply to received acoustic signals in determining the current levels for the bone conduction device's transducer. For example, if the bone conduction device receives an audible signal at a sound pressure level at a particular frequency that would be at the threshold sound level for a person of normal hearing, the bone conduction device will generate a current level at the threshold level for the recipient at this frequency. The bone conduction device's transducer may then use this current to apply stimulation such that the recipient hears the received audible signal at this frequency at the threshold level for the recipient. In embodiments using such a gain curve, data transformer 704 may generate and provide to bone conduction device, a table of gains per frequency, a transfer function for use by a amplifier of the bone conduction device, or any other suitable data that bone conduction device 401 may use to apply such a gain curve. Further, in an embodiment, data transformer 704 may generate and provided to bone conduction device a gain curve based on the threshold levels, and a comfort level curve providing the maximum current level per frequency to be used by the bone conduction device 401.

In another embodiment, the dynamic range parameters (e.g., threshold and comfort levels) may be measured in terms of sound pressure (e.g., dB), as noted above. In such an embodiment, data transformer 704 may transform the dynamic range parameters from the acoustic domain to the current levels for the bone conduction device 401. For example, the dynamic range parameters (e.g., threshold and comfort levels) may be obtained by providing a known acoustic signal to the recipient 402 and the intensity of this acoustic signal adjusted to measure the intensity. In an embodiment, data transformer 704 may determine a gain curve using the measured threshold sound pressure levels. As discussed above, this gain curve may be such that bone conduction device 401 applies a gain to all received audible signals. And, the gain applied per frequency is such that a sound at a threshold level for a person of normal hearing will be amplified to the threshold level for the recipient. It should be noted that although for explanatory purposes these gain curves are discussed with reference to a person of normal hearing, in other embodiments the gain curves may be determined based on other information, such as threshold levels for a particular population of people, etc.

Further, in an embodiment, data transformer 704 may convert these measured sound pressure levels to current levels used by the transducer module of the bone conduction device in applying stimulation to recipient 402. For example, data transformer 704 may store information that may be used to map a sound pressure level to a particular current level. This stored information may be different for different types of bone conduction devices. As such, audiologist 404 using the user interface may provide fitting system 406 with information specifying the type of bone conduction device, as well as, for example, any variable parameters for the bone conduction device, such as, for example, the volume or gain to which the bone conduction device was set during the measurements. Or, for example, fitting system 406 and bone conduction device 401 may communicate via link 408 such that fitting system 406 may be able to obtain this information directly from bone conduction device 401. Further, in an embodiment employing sound pressure levels, data transformer 704 may generate and provide to the bone conduction device a gain curve using the measured threshold levels, and a maximum current level curve by converting the measured sound pressure current levels to maximum current levels. It should be noted, that in certain embodiments, the bone conduction device may be calibrated prior to measuring the dynamic range parameters to help improve the accuracy of the MAP data generated by data transformer 704.

As noted above, the MAP data 422 generated by data transformer 704 may include, for example, various curves, such as gain versus frequency and maximum current level versus frequency, one or more tables specifying gain versus frequency and maximum current level versus frequency, a transfer function for use by an amplifier in applying a gain versus frequency curve, etc. Data transformer 704 may package this MAP data 422 in any form suitable for use by bone conduction device 401.

After receiving MAP data 422 from fitting system 406, bone conduction device 401 may store and use MAP data 422 in providing stimulation to recipient 402. The following provides a description of an exemplary embodiment of a mechanism bone conduction device 401 may use in applying stimulation using MAP data 422. In this example, MAP data 422 comprises a gain curve for applying a gain to all signals sound signal received by bone conduction device 401. As discussed above, this gain curve may comprise the gain to be applied to bring a received acoustic signal that is at the threshold sound pressure level for a person of normal hearing so that the bone conduction device 401 generates stimulation at the threshold current level for the recipient 402. Additionally, in this example, the MAP data 422 may further comprise a curve specifying the maximum comfortable current level per frequency for providing stimulation.

Referring back to FIG. 2, bone conduction device 401 may receive an acoustic signal via sound input element 202. Signal processor 240 may then retrieve the stored gain curve and apply a gain to the received signal in determining current levels for use in stimulating the recipient. Signal processor 240 may then determine if the current levels exceed the recipient's maximum comfort level by comparing the generated current levels against the stored maximum current level versus frequency curve. If the sound pressure of the received acoustic signal exceeds the comfort level, signal processor 240 may use various techniques to maintain the signals below the recipients comfort level.

Figure 8A:
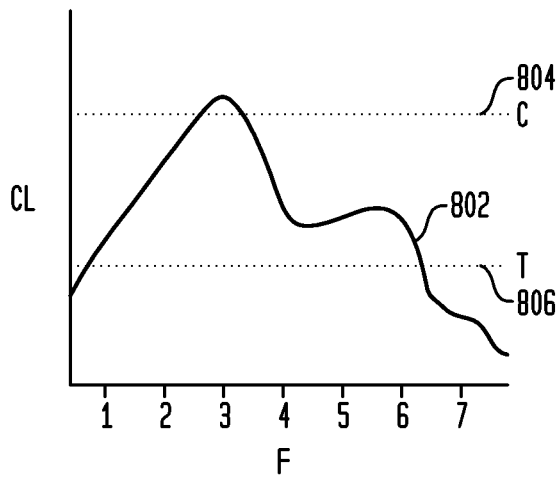
FIG. 8A is a waveform of an exemplary signal that includes frequencies that exceed a recipient's comfort level, in accordance with embodiments of the present invention.

FIG. 8A illustrates an exemplary signal that includes frequencies that exceed a recipients comfort level. In FIG. 8A, the X-axis corresponds to frequency (F) and the Y-axis corresponds to energy (E), which may be in terms of current level. FIG. 8A further illustrates the recipient's comfort level 804 and threshold level 806. For simplicity, the threshold and comfort levels are illustrates as constant across all frequencies. As illustrated, curve 802 is initially between the threshold and comfort levels, then rises above the comfort level. After which, the curve falls back below the comfort level.

Figure 8B:
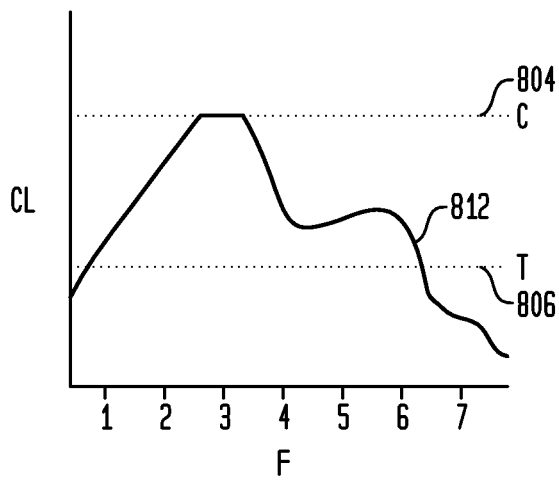
FIG. 8B is a waveform illustrating when a signal processor clips the signal when the signal exceeds the recipient's comfort level, in accordance with embodiments of the present invention.

FIG. 8B illustrates an embodiment in which signal processor simply clips the signal if the signal exceed the recipient's comfort level. For example, as illustrated, curve 812 is identical to curve 802, but has been clipped at frequencies exceeding the recipient's maximum comfort level. Thus, as illustrated, curve 812 is equal to the maximum comfort level for frequencies in which curve 802 exceeded the recipient's maximum comfort level. Signal processor 240 may then simply use the current levels from the clipped curve 812 in providing stimulation to the recipient.

Figure 8C:
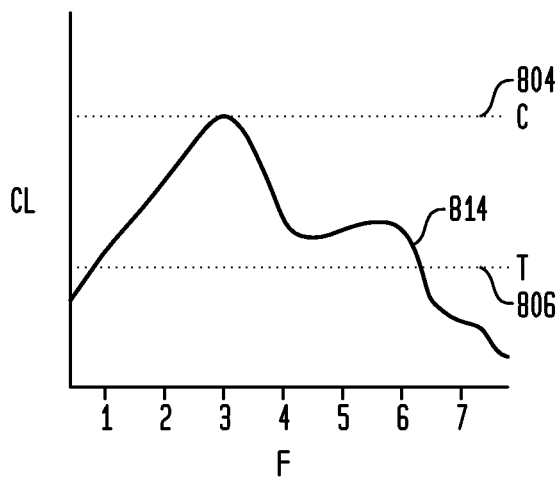
FIG. 8C is a waveform illustrating an alternative embodiment in which the signal processor scales the signal when it falls above the comfort level of the recipient, in accordance with embodiments of the present invention.

FIG. 8C illustrates an alternative embodiment in which the signal processor 204 scales the signal if it falls above the comfort level. For example, signal processor 240 may determine if the determined current level curve 802 exceeds the maximum comfort level 804 for any frequency. If so, signal processor 240 may determine the frequency with the peak amplitude, or, for example, the frequency with the current level that exceeds the comfort level by the most significant amount. Signal processor 240 may then divide the comfort level for this determined frequency by the pre-scaled current level for the frequency to obtain a multiplier (M). That is, M=C/S, where M is the multiplier, C is the comfort level for the frequency, and S is the calculated current level prior to scaling. Signal processor 240 may then multiply the pre-scaled current levels for each of the frequency bands by the calculated multiplier. This has the effect of scaling down curve 802 to produce a scaled down curve 814. Signal processor 240 may then use the scaled down current levels 814 in applying stimulation.

It should be noted that this is but one example of how a bone conduction device may use dynamic range parameters such as threshold and comfort levels to map a received acoustic signal to an intensity of the vibration to be applied by the bone conduction device, and in other implementations other mechanisms may be used.

Various implementations of the subject matter described, such as the embodiment of FIG. 7, be realized using digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, systems are also described herein that may include a processor and a memory coupled to the processor. The memory may include one or more programs that cause the processor to perform one or more of the operations described herein.

All documents, patents, journal articles and other materials cited in the present application are hereby incorporated by reference herein.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method comprising:
providing a test signal to a recipient of a bone conduction device using an acoustic fitting system;
receiving a response from the recipient to the provided test signal;
determining a dynamic range parameter based on the response;
determining map data for the bone conduction device using the determined dynamic range parameter; and
providing the map data to the bone conduction device for use by the bone conduction device in providing stimulation to the recipient.

2. The method of claim 1, wherein the dynamic range parameter comprises:
one or more of threshold level and comfort level.

3. The method of claim 2, wherein the bone conduction device is configured to provide stimulation over a plurality of frequencies, the method further comprising:
determining a threshold level for at least one of the frequencies, wherein the threshold level corresponds to a minimum intensity of stimulation at which the recipient perceives sound in response to the provided test signal; and
wherein determining map data comprises:
determining the map data using the determined threshold level.

4. The method of claim 3, further comprising:
determining a comfort level for the at least one of the frequencies; and
wherein determining the map data comprises:
determining the map data using the determined comfort level.

5. The method of claim 3, further comprising:
determining a comfort level for the at least one of the frequencies,
wherein determining the map data comprises:
determining the map data using the determined comfort level.

6. The method of claim 1, further comprising:
enabling the bone conduction device to clip or scale down a stimulation signal if the stimulation signal exceeds a threshold of the map data provided to the bone conduction device.

7. The method of claim 1, further comprising the action of:
transforming the map data from a domain of the acoustic fitting system to a domain of the bone conduction device.

8. The method of claim 1, wherein:
the response is a verbal response from the recipient.

9. The method of claim 1, wherein:
wherein the action of providing the test signal to the recipient entails providing the bone conduction device instructions to produce a vibration, wherein the produced vibration corresponds to the provided test signal.

10. The method of claim 1, wherein:
wherein the action of providing the test signal to the recipient entails providing the bone conduction device with an acoustic signal from a speaker, wherein the speaker is part of the acoustic fitting system, wherein the bone conduction device processes the acoustic signal to provide stimulation to the recipient, and wherein the provided stimulation corresponds to the provided test signal.

11. The method of claim 1, wherein:
wherein the action of providing the test signal to the recipient entails providing the bone conduction device with an acoustic signal from a speaker located away from the recipient and away from the bone conduction device, wherein the speaker is part of the acoustic fitting system, wherein the bone conduction device processes the acoustic signal to provide stimulation to the recipient, and wherein the provided stimulation corresponds to the provided test signal.

12. The method of claim 1, further comprising:
providing a second test signal to the recipient of the bone conduction device at a different intensity than that previously used using the acoustic fitting system;
receiving a second response from the recipient to the provided second test signal, wherein
the action of determining the dynamic range parameter is based on the response and the second response.

13. The method of claim 1, further comprising using the bone conduction device with the provided map data to evoke a hearing percept without the acoustic fitting system.

14. The method of claim 1, wherein a fitting system is utilized to provide the map data to the bone conduction device, wherein the fitting system is in signal communication with the bone conduction device, and wherein the bone conduction device is configured to be worn away from a location of the fitting system and used to evoke a hearing percept.

15. The method of claim 1, wherein at least a portion of the bone conduction device includes a component anchored to bone of the recipient beneath skin of the recipient.

16. A fitting system for fitting a bone conduction device for a recipient, comprising:
a user interface configured to provide data and receive input;
a test signal generator configured to provide the recipient with a test signal generated in response to said input, wherein the user interface is further configured to receive a response regarding the recipient's perception to the test signal;
a controller configured to determine a dynamic range parameter based on the response to the applied test signal, and further configured to determine map data for the bone conduction device using the determined dynamic range parameter; and
an interface configured to provide the bone conduction device with the determined map data for use by the bone conduction device in providing stimulation to the recipient.

17. The fitting system of claim 16, further comprising:
a data transformer configured to generate one or more curves based on the determined dynamic range parameter; and
wherein the controller is further configured to provide map data comprising the one or more curves to the bone conduction device via the interface.

18. The fitting system of claim 16, wherein the test signal generator is configured to generate an instruction for the bone conduction device to apply stimulation at a particular intensity.

19. The fitting system of claim 16, wherein the dynamic range parameter is selected from the set of a threshold and a comfort level.

20. The fitting system of claim 19, wherein the bone conduction device is configured to provide stimulation over a plurality of frequencies, and wherein the controller is further configured to determine a threshold level for at least one of the frequencies and determine the map data using the determined threshold level, wherein the threshold level corresponds to a minimum intensity of stimulation at which the recipient perceives sound in response to the provided test signal.

21. The fitting system of claim 20, wherein the controller is further configured to determine a comfort level for the at least one of the frequencies and determine the map data using the determined comfort level.

22. The fitting system of claim 16, where the interface configured to provide the bone conduction device with the determined map data is configured to enable the bone conduction device to clip or scale down a stimulation signal if the stimulation signal exceeds a threshold of the map data provided to the bone conduction device.

23. The fitting system of claim 16, wherein:
the test signal provided by the test signal generator is an acoustic test signal.

24. The fitting system of claim 16, further comprising:
a bone conduction hearing prosthesis corresponding to the bone conduction device wherein the bone conduction device is separate from the test signal generator.

25. A fitting system comprising:
means for providing a test signal to a recipient of a bone conduction device using an acoustic fitting system;
means for receiving a response from the recipient to the provided test signal;
means for determining a dynamic range parameter based on the response;
means for determining map data using the determined dynamic range parameter; and
means for transforming the map data from a domain of the acoustic fitting system to a domain of the bone conduction device; and
means for providing the map data to the bone conduction device for use by the bone conduction device in providing stimulation to the recipient.

26. The fitting system of claim 25, wherein the bone conduction device is configured to provide stimulation over a plurality of frequencies, the fitting system further comprising:
means for determining a threshold level for at least one of the frequencies, wherein the threshold level corresponds to a minimum intensity of stimulation at which the recipient perceives sound in response to the provided test signal; and
wherein the means for determining map data comprises:
means for determining the map data using the determined threshold level.

27. The fitting system of claim 25, further comprising the bone conduction device, wherein the bone conduction device is configured to evoke a hearing percept without the means for providing a test signal.

* * * * *